United States Patent
Monir et al.

(10) Patent No.: US 11,083,517 B2
(45) Date of Patent: Aug. 10, 2021

(54) ENHANCING EFFICIENCY OF REPEAT ABLATION BY MERGING CURRENT AND PREVIOUS MAPS

(71) Applicants: Biosense Webster (Israel) Ltd., Yokneam (IL); George Monir, Maitland, FL (US)

(72) Inventors: George Monir, Maitland, FL (US); Aharon Turgeman, Zichron Ya'acov (IL); Tal Haim Baron, Kiryat Tivon (IL); Gal Hayam, Tivon (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 361 days.

(21) Appl. No.: 15/811,856

(22) Filed: Nov. 14, 2017

(65) Prior Publication Data

US 2018/0199990 A1   Jul. 19, 2018

Related U.S. Application Data

(60) Provisional application No. 62/447,936, filed on Jan. 19, 2017.

(51) Int. Cl.
  *A61B 18/14* (2006.01)
  *A61B 34/20* (2016.01)
  (Continued)

(52) U.S. Cl.
  CPC .......... *A61B 18/1492* (2013.01); *A61B 34/20* (2016.02); *A61B 5/062* (2013.01);
  (Continued)

(58) Field of Classification Search
  CPC .... A61B 2034/2051; A61B 2034/2063; A61B 2034/2065; A61B 2018/00356; A61B 2018/00577
  See application file for complete search history.

(56) References Cited

U.S. PATENT DOCUMENTS

| | | |
|---|---|---|
| 7,517,318 B2 | 4/2009 | Altmann et al. |
| 7,855,723 B2 | 12/2010 | Preiss et al. |

(Continued)

FOREIGN PATENT DOCUMENTS

| | | |
|---|---|---|
| WO | 2011/135482 A1 | 11/2011 |
| WO | 2016/014949 A1 | 1/2016 |

OTHER PUBLICATIONS

Salas, Atrial mapping during pulmonary vein pacing: a novel maneuver to detect and close residual conduction gaps in an ablation line 2016, J of Card Electrophysio, vol. 47, pp. 299-307 (Year: 2016).*

(Continued)

*Primary Examiner* — Linda C Dvorak
*Assistant Examiner* — Annabeth E Rodriguez
(74) *Attorney, Agent, or Firm* — Notaro, Michalos & Zaccaria P.C.

(57) ABSTRACT

A method for cardiac treatment, which includes acquiring and saving an initial map of a chamber of a heart of a patient in an initial ablation procedure, with locations of ablation lesions marked on the initial map. In preparation for a redo ablation procedure, subsequent to the initial ablation procedure, a current map of the chamber is acquired, the initial map is registered with the current map, and the locations of the ablation lesions from the registered initial map are marked and displayed on the current map.

9 Claims, 7 Drawing Sheets

(51) Int. Cl.
*A61B 18/00* (2006.01)
*A61B 34/10* (2016.01)
*A61B 5/06* (2006.01)
*A61B 90/00* (2016.01)

(52) U.S. Cl.
CPC ........... *A61B 2018/00357* (2013.01); *A61B 2018/00577* (2013.01); *A61B 2018/00839* (2013.01); *A61B 2018/00875* (2013.01); *A61B 2018/00988* (2013.01); *A61B 2034/107* (2016.02); *A61B 2034/2051* (2016.02); *A61B 2034/2063* (2016.02); *A61B 2034/2065* (2016.02); *A61B 2090/065* (2016.02)

(56) References Cited

U.S. PATENT DOCUMENTS

| | | |
|---|---|---|
| 7,918,793 B2 | 4/2011 | Altmann et al. |
| 8,320,711 B2 | 11/2012 | Altmann et al. |
| 8,320,771 B2 | 11/2012 | Altmann et al. |
| 8,900,225 B2 | 12/2014 | Bar-Tal et al. |
| 9,364,251 B2 | 6/2016 | Aljuri et al. |
| 9,439,735 B2 | 9/2016 | Guttman et al. |
| 2003/0093067 A1 | 5/2003 | Panescu |
| 2006/0241445 A1* | 10/2006 | Altmann ............... A61B 8/12 600/443 |
| 2007/0049817 A1 | 3/2007 | Preiss et al. |
| 2007/0167784 A1 | 7/2007 | Shekbar et al. |
| 2009/0268955 A1 | 10/2009 | Koolwal et al. |
| 2010/0016712 A1 | 1/2010 | Bar-Tal et al. |
| 2011/0130648 A1 | 6/2011 | Beeckler et al. |
| 2011/0160569 A1 | 6/2011 | Cohen et al. |
| 2012/0035459 A1 | 2/2012 | Revishvili et al. |
| 2013/0066193 A1 | 3/2013 | Olson et al. |
| 2013/0072773 A1* | 3/2013 | Wu .................. A61B 6/12 600/373 |
| 2013/0116681 A1 | 5/2013 | Zhang |
| 2013/0296845 A1* | 11/2013 | Bar-Tal ................ A61N 1/06 606/34 |
| 2014/0107512 A1 | 4/2014 | Greenspan |
| 2014/0200467 A1 | 7/2014 | Strom et al. |
| 2016/0120426 A1 | 5/2016 | Urman et al. |
| 2018/0042671 A1* | 2/2018 | Gelbart ............... A61B 18/082 |

OTHER PUBLICATIONS

Extended European Search Report for corresponding European patent application No. EP 18152349.9, dated Jun. 13, 2018.
U.S. Appl. No. 62/447,936, filed Jan. 19, 2017.

* cited by examiner

ENHANCING EFFICIENCY OF REPEAT ABLATION BY MERGING CURRENT AND PREVIOUS MAPS

CROSS-REFERENCE TO RELATED APPLICATION

This application claims the benefit of U.S. Provisional Patent Application 62/447,936, filed Jan. 19, 2017, which is incorporated herein by reference.

FIELD OF THE INVENTION

The present invention relates generally to systems and methods for-invasive medical treatment, and specifically to tracking and evaluating such treatment.

BACKGROUND

Minimally-invasive intracardiac ablation is the treatment of choice for various types of arrhythmias. To perform such treatment, the physician typically inserts a catheter through the vascular system into the heart, brings the distal end of the catheter into contact with myocardial tissue in areas of abnormal electrical activity, and then energizes one or more electrodes at or near the distal end in order to create tissue necrosis.

A number of systems for intracardiac ablation therapy are commercially available, such as the CARTO® system offered by Biosense Webster Inc. (Irvine, Calif.). CARTO tracks the position and operating parameters of the distal end of the catheter and displays this information electronically on a three-dimensional (3D) anatomical map of the heart. CARTO enables the system operator to electronically tag locations that have been ablated on the map and thus to keep track of the progress of the procedure.

These sorts of capabilities are described, for example, in U.S. Pat. No. 8,900,225, whose disclosure is incorporated herein by reference. This patent describes a method for performing a medical procedure in which a probe is brought into contact with an organ in a body of a patent. A map of the organ is displayed, and the location of the probe relative to the map is tracked. A therapy is applied via the probe at multiple tissue sites in the organ with which the probe is brought into contact. Stability of the contact between the probe and the tissue sites is assessed while applying the therapy. The map is automatically marked, responsively to the assessed stability, to indicate the tissue sites at which the therapy was applied.

Atrial fibrillation (AF) often stems from arrhythmogenic electrical activity originating in areas in and around the pulmonary veins. This condition can be treated by a pulmonary vein isolation (PVI) procedure, in which a catheter is inserted into the left atrium and ablates myocardial tissue around the ostia of the pulmonary veins, typically by applying radio frequency (RF) energy to create lesions in the tissue. The operating physician uses the catheter to create multiple overlapping ablation lesions, which form wide circumferential ablation (WCA) lines in the tissue around the pulmonary veins and thus interrupt any conductive pathways between the pulmonary veins and the atrium. This treatment can be carried out, for example, using the above-mentioned CARTO system, which is capable of both mapping the shape of and electrical activity in the heart and applying the RF energy to ablate the tissue. When successful, PVI by RF ablation (RFA) completely blocks the arrhythmogenic currents and thus permanently resolves the AF.

In many cases, however, AF recurs after treatment, sometimes long after the date of the original PVI procedure. This sort of recurrence of AF has been shown to be related in a significant percentage of patients to recurrence of conduction from the pulmonary veins to the left atrium. To treat and resolve the recurrence, the physician must once again insert a catheter into the left atrium and attempt to close the conduction gaps (CGs) that exist in the WCA lines with additional, new RFA lesions in the appropriate locations so as to completely isolate the PVs. This sort of repeat RFA procedure is known in the art as "redo ablation."

SUMMARY

Embodiments of the present invention that are described hereinbelow provide methods and systems for performing ablation procedures, and particularly for improving the ease and efficacy of redo ablation.

There is therefore provided, in accordance with an embodiment of the invention, a method for cardiac treatment, which includes acquiring and saving an initial map of a chamber of a heart of a patient in an initial ablation procedure, with locations of ablation lesions marked on the initial map. In preparation for a redo ablation procedure, subsequent to the initial ablation procedure, a current map of the chamber is acquired, the initial map is registered with the current map, and the locations of the ablation lesions from the registered initial map are marked and displayed on the current map.

In some embodiments, registering the initial map includes identifying at least one anatomical landmark in both the initial map and the current map, and aligning the at least one landmark identified in the initial map with a position of the at least one landmark identified in the current map. In a disclosed embodiment, the chamber is a left atrium of the heart, and the at least one landmark includes a carina between superior and inferior pulmonary veins connecting to the left atrium.

Additionally or alternatively, displaying the locations of the ablation lesions includes superimposing on the current map wide circumferential ablation (WCA) lines produced in the initial ablation procedure, and the redo ablation procedure includes ablating further tissue in the chamber at sites chosen to close at least one conduction gap in the WCA.

In a disclosed embodiment, the method includes sensing electrical activity in the chamber of the heart, and displaying an indication of the sensed electrical activity on the current map, showing a conduction gap between the ablation lesions. Additionally or alternatively, the redo ablation procedure includes ablating further tissue in the chamber, and the method includes marking and displaying on the current map the locations of further ablation lesions created by ablating the further tissue together with the ablation lesions from the registered initial map.

In some embodiments, the ablation lesions are produced by application of radio frequency (RF) energy to myocardial tissue in the chamber of the heart, and the initial map and the current map are acquired by inserting a probe into the chamber of the heart, and tracking coordinates of the probe while moving the catheter within the heart.

There is also provided, in accordance with an embodiment of the invention, a system for cardiac treatment, including a probe configured for insertion into a chamber of a heart of a patient. A processor is configured to receive an initial map of a chamber of a heart of a patient, acquired in an initial ablation procedure, with locations of ablation lesions marked on the initial map, and is coupled to acquire a current map of the chamber using the probe in preparation for a redo ablation procedure, subsequent to the initial ablation procedure, and to register the initial map with the current map and to mark and display on the current map the locations of the ablation lesions from the registered initial map.

There is additionally provided, in accordance with an embodiment of the invention, a computer software product, including a computer-readable medium in which program instructions are stored, which instructions, when read by a processor, cause the processor to receive an initial map of a chamber of a heart of a patient, acquired in an initial ablation procedure, with locations of ablation lesions marked on the initial map, and to acquire a current map of the chamber in preparation for a redo ablation procedure, subsequent to the initial ablation procedure, and to register the initial map with the current map and to mark and display on the current map the locations of the ablation lesions from the registered initial map.

The present invention will be more fully understood from the following detailed description of the embodiments thereof, taken together with the drawings in which:

DETAILED DESCRIPTION OF EMBODIMENTS

Overview

Figure 1:
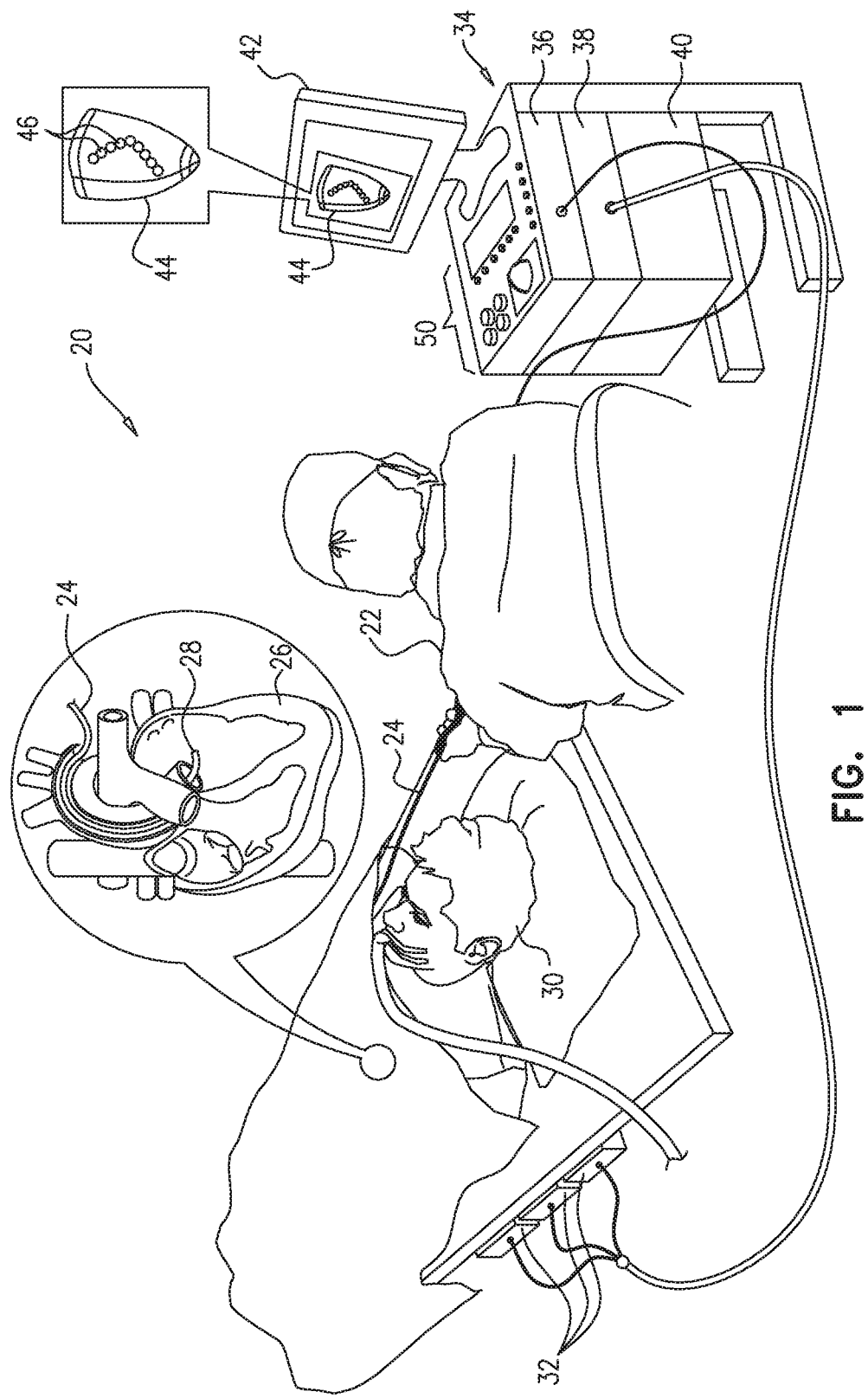
FIG. 1 is a schematic pictorial illustration of a system for intracardiac ablation, in accordance with an embodiment of the invention.

One of the challenges in a redo ablation procedure is to find the precise locations of the WCA lines made in the previous procedure, so that new RFA lesions can be placed exactly where necessary in order to achieve re-isolation of the pulmonary veins. For this purpose, it is desirable that data acquired during the previous mapping and ablation procedure be available during the redo ablation, and particularly that these earlier data be incorporated into the map of the atrium that the physician is currently viewing while performing the redo ablation. Although some existing mapping tools permit the user to superimpose and register different images of the heart, they do not enable the physician to view and make use of the mapping and ablation data, including the WCA lines, from a previous procedure on the current map. The inability to incorporate the previously-acquired map and ablation data in the current map results in unnecessary repetitions of RFA and prolongs procedure time.

More generally, physicians encounter these same sorts of challenges in treating various other rhythm disorders originating in different chambers of the heart, such as ventricular tachycardia (VT). Inability to use the mapping and ablation data acquired in previous sessions creates significant limitations. These data can be crucial in the redo cases for accurate targeting and/or evaluation of the previous ablation.

Embodiments of the present invention that are described herein provide novel techniques, implemented in software, for registering and superimposing a previously-acquired map and RFA data onto the current map that is in use by the physician in a redo ablation procedure. The registration and superimposition rely on accurate alignment of the previous and current maps, so that the inner surfaces of the heart chamber in the previous and current maps are precisely registered with one another, even when a long period (possibly on the order of a year or more) has elapsed between the previous and current procedures.

The alignment is typically based, inter alia, on matching anatomical landmarks, such as the carina-between superior and inferior pulmonary veins, which the inventors have found to facilitate accurate and reliable registration of the left atrium, or other fixed anatomical landmarks in other arrhythmias and chambers of the heart. For example, in other cardiac chambers, anatomical landmarks such as the coronary sinus, bundle of His, or superior and inferior venae cavae can be use individually or in combination for map registration and alignment. Thus, although the embodiments that are illustrated in the figures relate specifically to RFA treatment of atrial fibrillation in the left atrium, the principles of the present invention may similarly be applied in treatment of other conditions in the atria or ventricles, such as ventricular tachycardia.

Furthermore, although the embodiments described hereinbelow relate specifically to RFA, the principles of the present invention may similarly be applied, mutatis mutandis, in facilitating redo procedures using other ablation modalities that are known in the art, such as ultrasonic ablation or cryo-ablation.

Automatic registration, superimposition and visualization of previous map data and RFA lesion data on the current map in this manner eliminates any need for user involvement in reduplication of these data and has been found to facilitate and shorten redo ablation times. In effect, the redo ablation becomes an extension of the previous procedure. The ability to view the previous lesion set directly on the current map also helps the physician to understand the reasons for the failure of the previous procedure and thus improve future treatments.

System Description

FIG. 1 is a schematic, pictorial illustration of a cardiac mapping and ablation system 20, which operates in accordance with an embodiment of the invention. System 20 may be based, for example, on the above-mentioned CARTO system, with suitable additions to the system software. System 20 comprises a probe, such as a catheter 24, and a control console 34. In the embodiment described hereinbelow, catheter 24 is used in ablating sites of arrhythmias in one or more chambers of a heart 26 of a patient 30.

An operator 22, such as a cardiologist, inserts catheter 24 through the vascular system of patient 30 so that the distal end of the catheter enters a chamber of heart 26. Operator 22 advances the catheter so that an electrode 28 at the distal tip of the catheter engages endocardial tissue at desired ablation sites. Catheter 24 is typically connected by a suitable connector at its proximal end to console 34, and specifically to a radio frequency (RF) generator 36, which generates RF energy for transmission via catheter 24 to electrode 28. Operator 22 actuates RF generator 36 to ablate tissue at and/or around suspected sites of arrhythmia in the heart.

In this pictured embodiment, system 20 uses magnetic position sensing to determine position coordinates of the distal end of catheter 24 inside heart 26. For this purpose, a driver circuit 38 in console 34 drives field generators 32 to generate magnetic fields within the body of patient 30. Typically, field generators 32 comprise coils, which are placed below the patient's torso at fixed, known positions. These coils generate magnetic fields in a predefined working volume that contains heart 26. A magnetic field sensor (not shown) within the distal end of catheter 24 generates electrical signals in response to these magnetic fields. A signal processor 40 processes these signals in order to determine the position coordinates of the distal end of catheter 24, typically including both location and orientation coordinates, and tracking these coordinates in order to create a map of the interior surface of the heart. This method of position sensing is implemented in the above-mentioned CARTO system and is well known in the art. Alternatively or additionally, system 20 may use other methods of position sensing that are known in the art, such as ultrasonic or electrical impedance-based methods.

In addition, catheter 24 may comprise a force sensor (not shown) in its distal end, for measuring the contact force between the catheter tip and the wall of heart 26. The SmartTouch™ catheter developed by Biosense Webster Inc. for the CARTO system offers this sort of capability. A catheter of this sort is described, for example, in U.S. Patent Application Publication 2011/0130648, whose disclosure is incorporated herein by reference. The force measurement is useful in ensuring that electrode 28 is in sufficiently firm contact with the heart wall to effectively transfer RF energy and ablate the heart tissue. The force measurements can also be used by processor 40 in tagging ablation sites, as described below.

Processor 40 in console 34 typically comprises a general-purpose computer processor, with suitable front end and interface circuits for receiving signals from catheter 24 and for controlling and receiving inputs from the other components of console 34. Processor 40 may be programmed in software to carry out the functions that are described herein. The software may be downloaded to processor 40 in electronic form, over a network, for example, or it may be provided, alternatively or additionally, on tangible, non-transitory media, such as optical, magnetic or electronic memory media. Further alternatively or additionally, some or all of the functions of processor 40 may be carried out by dedicated or programmable digital hardware components.

Based on the signals received from catheter 24 and other components of system 20, processor 40 drives a display 42 to present operator 22 with a three-dimensional (3D) map 44 of heart 26. The map may indicate cardiac electrophysiological activity measured by catheter 24, as well as providing visual feedback regarding the position of the catheter in the patient's body and status information and guidance regarding the procedure that is in progress. Other parameters that may be measured by catheter 24 and by other elements of system 20 and may be shown on display 42 can include, for example, contact force between the catheter and heart tissue, electrical impedance of the heart tissue, local temperature, and RF power delivered through the catheter.

Processor 40 assesses the parameters that it receives from system 20 as indicators of the adequacy of ablation at each treated site in heart 26. When the ablation parameters at a given site meet certain predefined criteria, the processor automatically places a mark 46, also referred to as a "tag," on map 44 to indicate the site. The processor may vary the appearance of marks 46 (such as their color) in response to the parameters at each site. The criteria for automatic marking of the ablation sites may be preconfigured, or they may, alternatively or additionally, be set by operator 22, typically using user interface controls 50 and on-screen menus. Additionally or alternatively, operator 22 can use controls 50 to instruct processor to place marks 46 at ablation sites.

Although in the illustrated embodiment, catheter 24 is manipulated manually by operator 22, system 20 may alternatively or additionally comprise an automated mechanism (not shown) for maneuvering and operating the catheter within the body of patient 30. In such embodiments, processor 40 generates a control input for controlling the motion of catheter 24 based on the signals provided by the magnetic field sensor in the catheter and other system parameters, such as those mentioned above.

Methods of Operation

Figure 2:
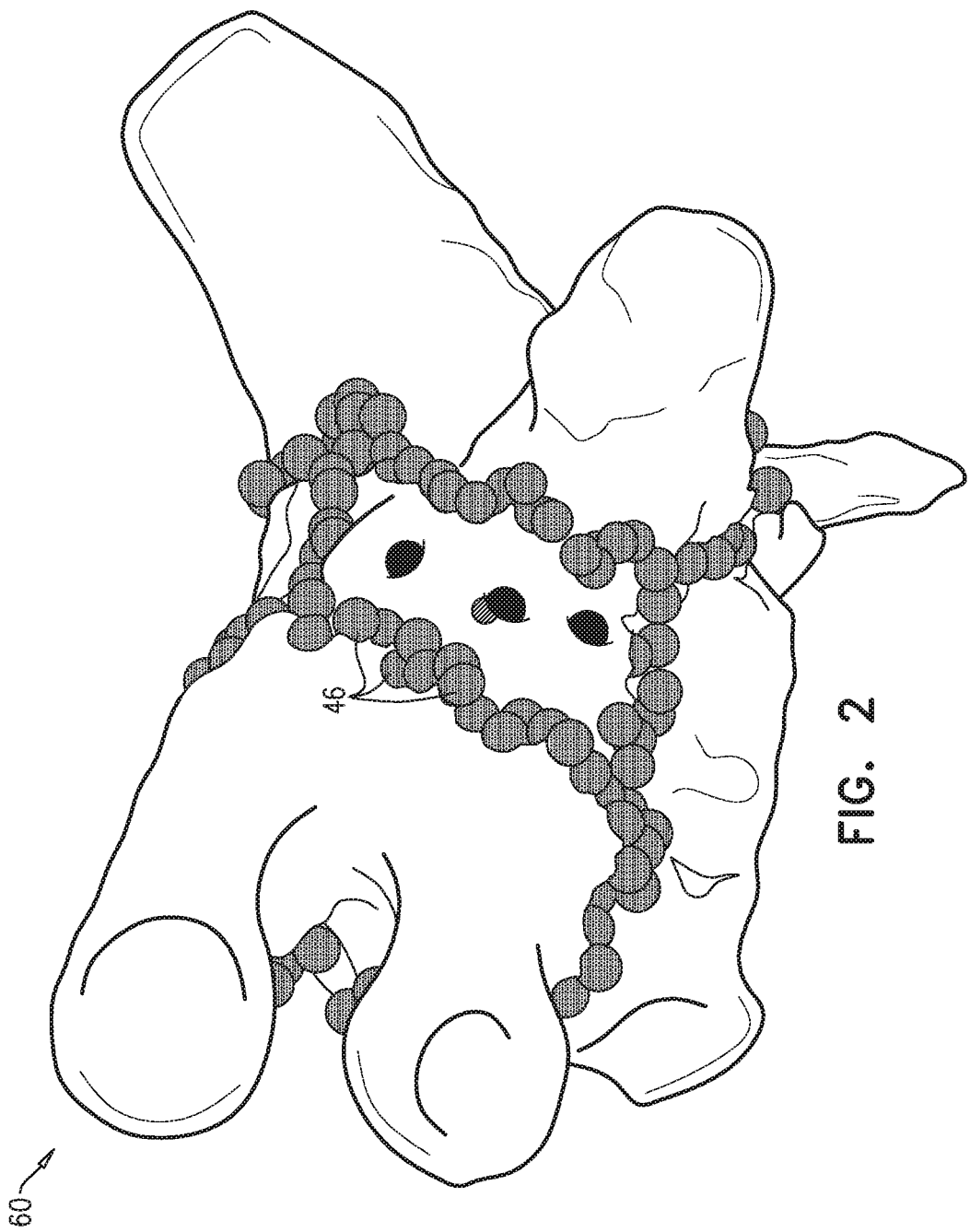
FIG. 2 is a schematic representation of a map of the left atrium of a patient at the conclusion of an initial ablation treatment, in accordance with an embodiment of the invention.
Figure 3:
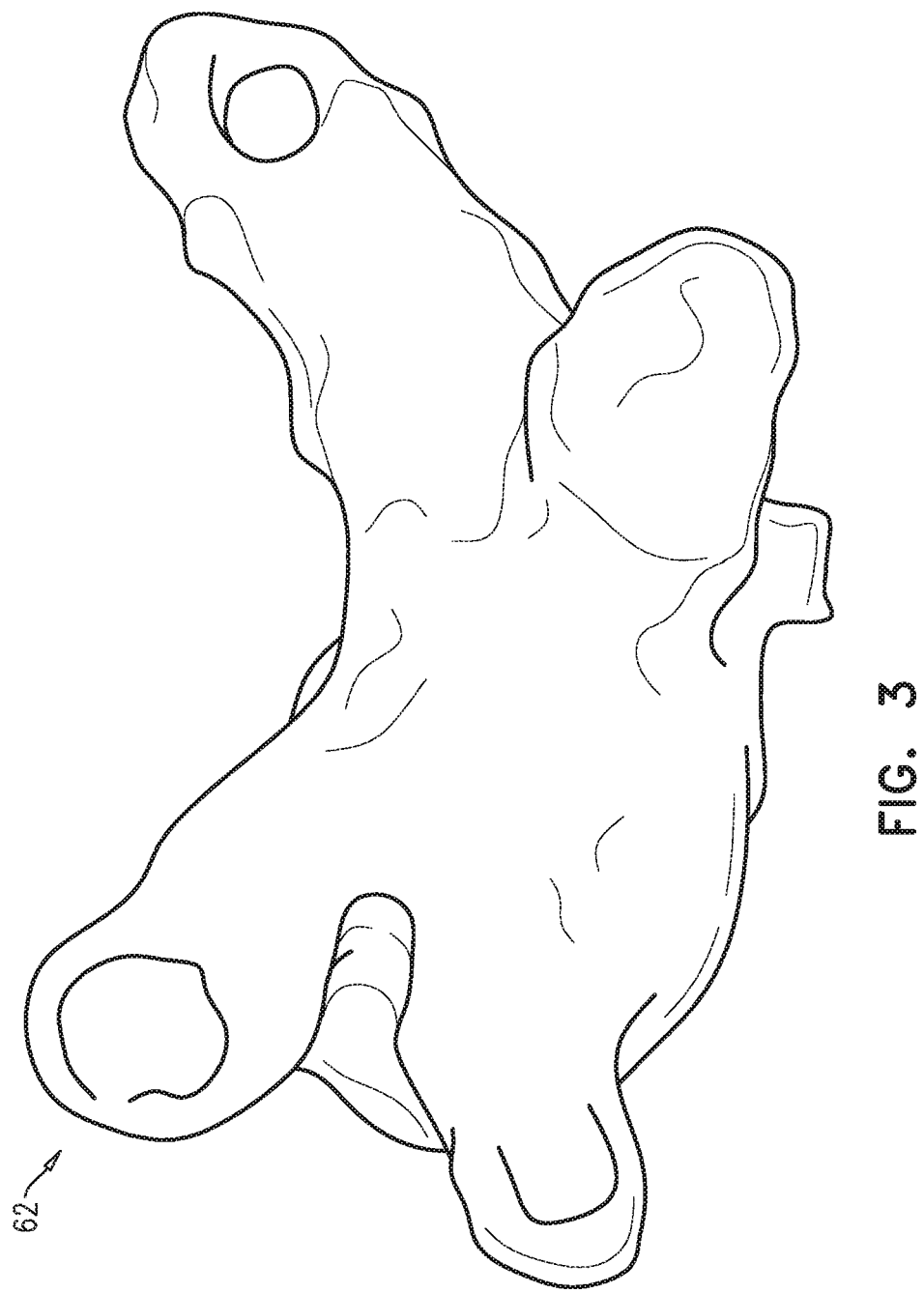
FIG. 3 is a schematic representation of a map of the left atrium shown in FIG. 2, produced just before beginning a redo ablation procedure, in accordance with an embodiment of the invention.

FIGS. 2 and 3 are schematic representations of maps 60 and 62, respectively, of the left atrium of a patient during an initial PVI treatment to treat AF, and a subsequent redo ablation treatment, in order to resolve a recurrence of the AF. These figures are reproductions of actual maps, taken from procedures performed about one year apart. The procedures were performed using a CARTO system, and maps 60 and 62 were acquired automatically by the system as the operating physician manipulated a mapping and ablation catheter within the heart. The markings shown on map 60 were likewise created by the CARTO system and include Visitag™ marks 46 (which appear in the figures as small balls superimposed on the heart surface), which indicate RFA locations and may also hold data regarding ablation parameters at each location.

Map 60 shows the left atrium at the conclusion of the initial ablation treatment, while map 62 shows the same atrium just before beginning the redo ablation procedure (a year later). Visitag marks 46 on map 60 (and/or other RFA marks) show the locations of circumferential WCA lines that were ablated by the physician in the initial treatment, around the ostia of the pulmonary veins. No such marks appear initially on map 62, thus making it difficult for operator 22 to identify during the redo procedure which locations were already ablated in the previous procedure.

Figure 4:
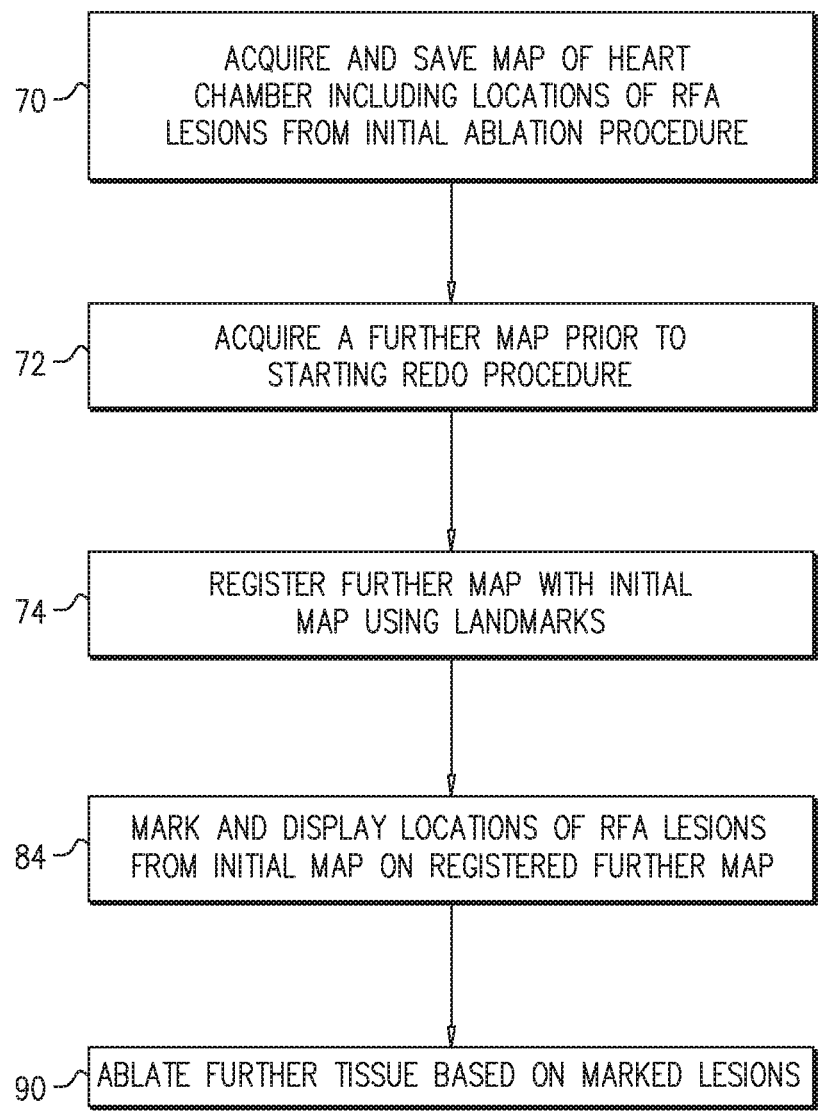
FIG. 4 is a flow chart that schematically illustrates a method for performing a redo ablation procedure, in accordance with an embodiment of the invention.

FIG. 4 is a flow chart that schematically illustrates a method for performing a redo ablation procedure, while automatically transferring the locations of RFA lesions from a previous map (such as map 60) to the current map (such as map 62), in accordance with an embodiment of the invention. The method is described, for the sake of concreteness and clarity, with reference to the elements of system 20 (FIG. 1) and to a sequence of example maps of the left atrium, shown in FIGS. 2, 3 and 5-7. Alternatively, as noted earlier, the method can be carried out using other sorts of ablation systems and can be applied to other chambers of the heart, as well.

At a preliminary step 70, in an initial ablation procedure, prior to the present redo ablation, console 34 acquired and saved an initial map of the heart chamber, with locations of RFA lesions marked in the initial map, as shown in FIG. 2, for example. Before beginning the subsequent redo ablation procedure, console 34 acquires a current map of the chamber, such as map 62, illustrated in FIG. 3, at a map acquisition step 72. Console 34 then registers the initial map with the current map, at a map registration step 74. This registration can be performed by identifying one or more anatomical landmarks in both the initial map and the current map, and aligning the landmarks identified in the initial map with the positions of the same landmarks identified in the current map.

Figure 5:
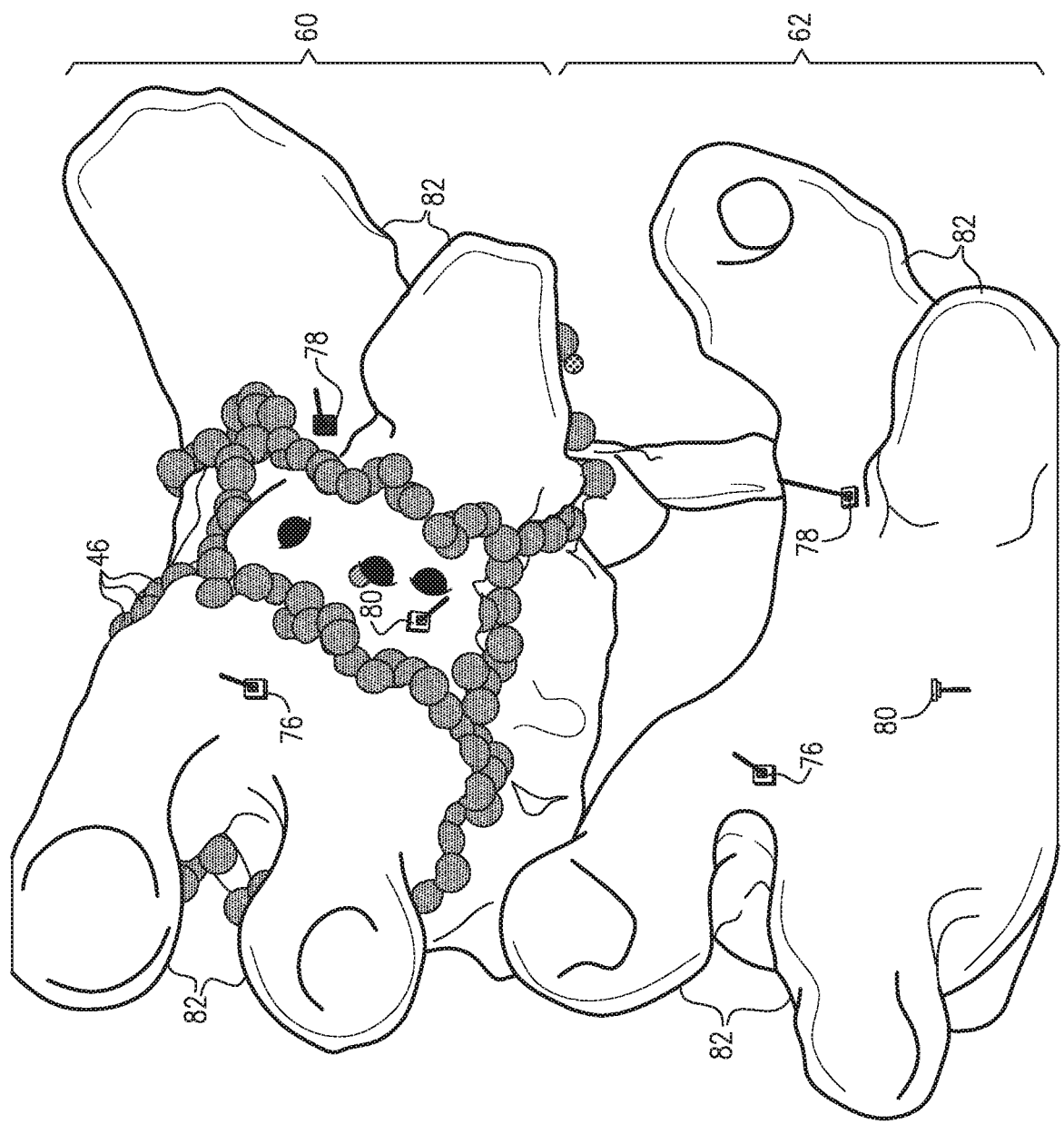
FIG. 5 is a schematic representation of the maps of FIGS. 2 and 3, illustrating landmarks used in registering the maps with one another, in accordance with an embodiment of the invention.

FIG. 5 is a schematic representation of maps 60 and 62 (from FIGS. 2 and 3), illustrating landmarks 76, 78, 80 that are used in registering the maps, in accordance with an embodiment of the invention. Maps 60 and 62 are shown side by side in FIG. 5 as an aid to visualization. In this example, the carina between superior and inferior pulmonary veins 82 on the left and right sides of the left atrium serve as landmarks 76 and 78. These carina may conveniently be found automatically by geometrical analysis of maps 60 and 62, with or without operator assistance. Landmark 80 is chosen in the present example to be the apex of an isosceles triangle, with its base drawn between landmarks 76 and 78. Console 34 aligns landmarks 76, 78 and 80 in maps 60 and 62 and thus registers the initial map with the map surface in the current map.

Returning now to FIG. 4, based on the registration between the initial and current maps at step 74, console 34 marks and displays on the current map (i.e., on map 62 in the present example) the locations of the RFA lesions from the initial map, at a marking step 84. In this manner, the Visitag and/or other RFA marks corresponding to the WCA lines from the initial map are displayed at the precise corresponding locations on the current map. Operator 22 manipulates catheter 24 and actuates system 20 to ablate further tissue in the left atrium, at an ablation step 90. The operator (or system 20, operating automatically) can use the markings on the current map to choose ablation sites in proximity to the previous RFA lesions, and specifically to close any gaps that have opened in the WCA lines that were ablated previously.

Figure 6:
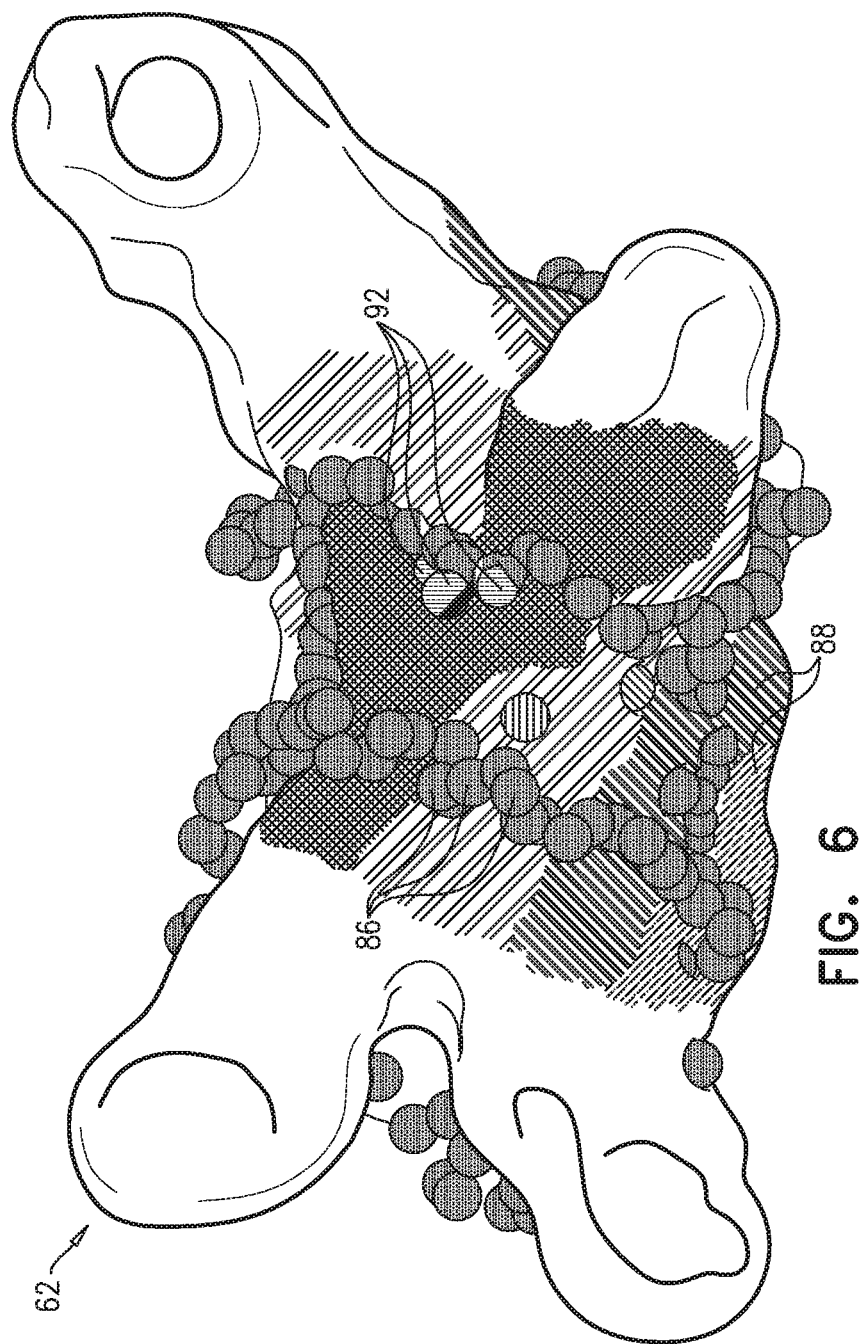
FIGS. 6 and 7 are schematic representations of a map of the left atrium, with tags representing both previous and current ablation lesions, in accordance with an embodiment of the invention.
Figure 7:
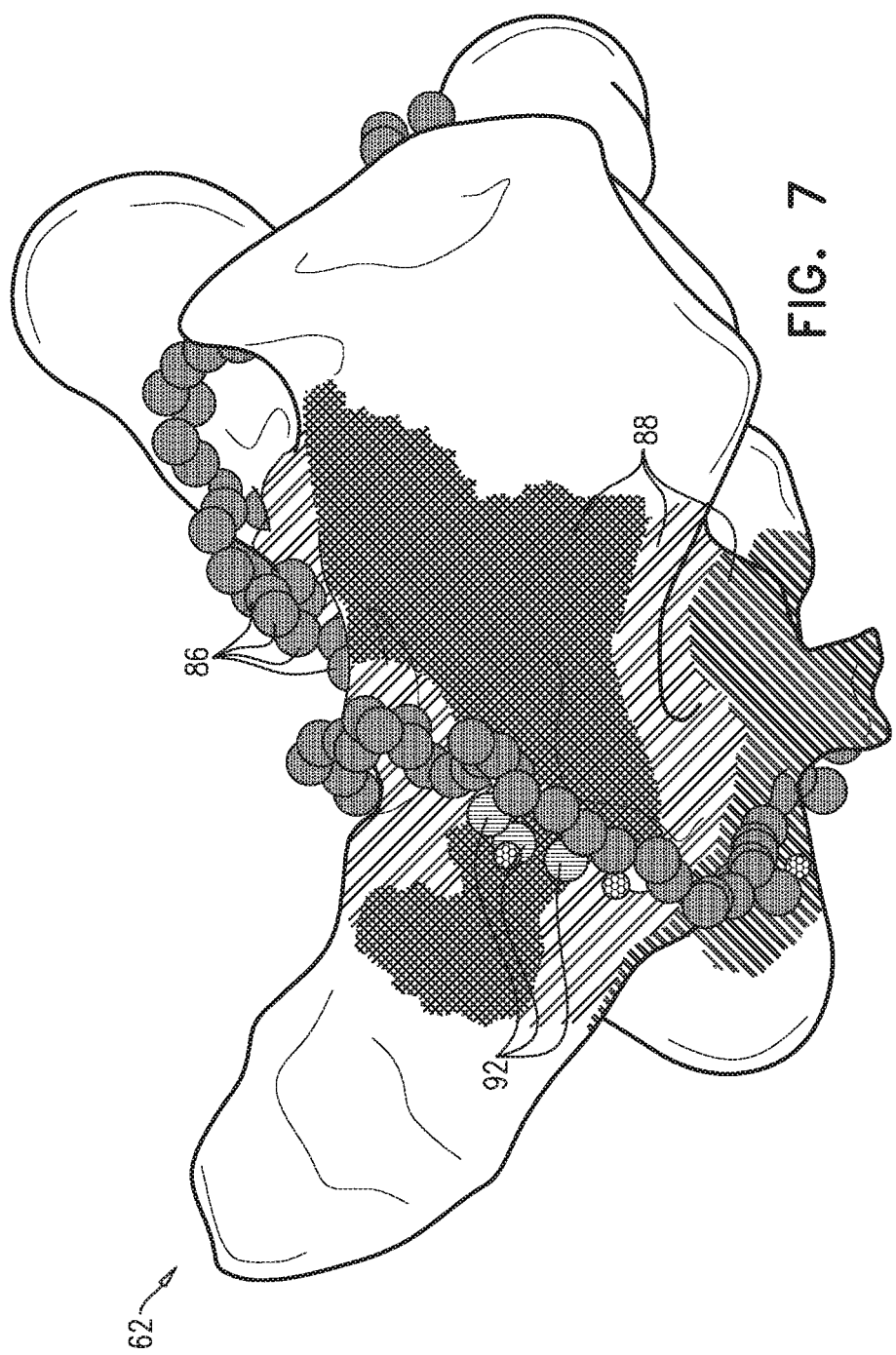

FIGS. 6 and 7 are schematic representations of map 62, seen from two different angles, illustrating the operations carried out in steps 84 and 90, in accordance with an embodiment of the invention. Map 62 now includes both marks 86, representing ablation lesions made previously in the initial ablation procedure, and new marks 92 at the sites ablated in the current procedure. Marks 86 are transferred to map 62 from map 60 on the basis of the registration performed at step 74, while marks 92 are added to map 62 by console 34 as the corresponding sites are ablated in step 90.

FIGS. 6 and 7 also show an electrical activity map 88, which is superimposed on the surface of map 62. System 20 acquires this electrical activity map by sensing electrical activity in the left atrium, using catheter 24 or another sensing catheter (not shown). Electrical activity map 88 gives an indication of the electrical activity in the atrial wall, which is useful, together with marks 86 showing past RFA locations, in visualizing the locations of gaps in the WCA lines, where arrhythmogenic electrical activity "leaks through." The operator thus can create new RFA lesions at locations that are chosen in order to close the gaps and can observe the effect of these new lesions (indicated by the corresponding marks 92) on the electrical activity shown in map 88.

Clinical Results

The inventors performed a clinical study to examine the efficacy of utilizing the present techniques in reducing procedure and RFA time in redo PVI. Software running on the CARTO system was used in incorporation of a previously-acquired map and RFA lesion marks for use in the current active map.

Fifty patients (Pts) presenting for redo RFA for recurrent atrial fibrillation were enrolled in the study. Group (GR) 1 included 23 Pts who had prior maps that could be merged into the current map. GR 2 included the 27 Pts without available prior maps. Both groups underwent CARTO 3D mapping of the left atrium and pulmonary veins to create an anatomical structural shell. In GR 1, the prior map was merged into the current, active map. Electrical activity maps (specifically, activation maps) were created to localize conduction gaps (CGs), and focal RFA was delivered only to target the CGs on the WCA lines in order to achieve pulmonary vein isolation (PVI). In GR 2, standard methods for CG localization and guiding RFA to achieve PVI were used.

In both groups the following data were collected and compared: RFA time (RFA-T), duration to complete RFA (RFA-D), and total procedure duration (TP-D) to achieve PVI per PV pair (PVP). The TP-D is defined as the sum of mapping time and RFA-D.

Results: Group 1 had a statistically significant reduction of the measured procedure parameters (minutes)), as shown in Table I below.

TABLE I

| | STUDY RESULTS | | | |
|---|---|---|---|---|
| | PVP with CG | RFA-T/PVP | RFA-D/PVP | TP-D/PVP for PVI |
| GR 1 | 19 | 3.5 ± 2.1 | 4.8 ± 4.2 | 7.7 ± 7.5 |
| GR 2 | 32 | 19.3 ± 10.2 | 38.4 ± 39.3 | 40.7 ± 39.8 |
| Reduction | | 82% | 88% | 81% |
| P value | | 0.002 | <0.001 | <0.001 |

Conclusion: Redo PVI using the techniques described above facilitates accurate localization of conduction gaps and significantly reduces RFA and procedure time to achieve PVI.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for cardiac treatment, comprising:
   in an initial ablation procedure, acquiring and saving an initial map of a chamber of a heart of a patient with locations of ablation lesions marked on the initial map; and
   in preparation for a redo ablation procedure, subsequent to the initial ablation procedure:

acquiring a current map of the chamber;
registering the initial map with the current map; and
marking and displaying on the current map the locations of the ablation lesions from the registered initial map,
wherein registering the initial map comprises identifying at least one anatomical landmark in both the initial map and the current map, and aligning the at least one landmark identified in the initial map with a position of the at least one landmark identified in the current map,
wherein the chamber is a left atrium of the heart, and the at least one landmark comprises a carina between superior and inferior pulmonary veins connecting to the left atrium,
wherein displaying the locations of the ablation lesions comprises superimposing on the current map wide circumferential ablation (WCA) lines produced in the initial ablation procedure, and wherein the redo ablation procedure comprises ablating further tissue in the chamber at sites chosen to close at least one conduction gap in the wide circumferential ablation (WCA) lines,
further comprising sensing electrical activity in the chamber of the heart,
further comprising generating an electrical activity map and superimposing the electrical activity map on the surface of the current map,
wherein the electrical activity map is generated by sensing electrical activity in the left atrium using a probe,
wherein the electrical activity map provides information regarding the electrical activity,
further comprising employing the information regarding the electrical activity in the atrial wall in connection with the at least one anatomical landmark in both the initial map and the current map to determine locations of gaps in the wide circumferential ablation (WCA) lines,
further comprising creating further ablation lesions at locations chosen in order to close the gaps in the wide circumferential ablation (WCA) lines, and
further comprising visualizing an effect of the further ablation lesions on the electrical activity in the atrial wall.

2. The method according to claim 1, wherein the redo ablation procedure comprises ablating further tissue in the chamber, and wherein the method comprises marking and displaying on the current map the locations of further ablation lesions created by ablating the further tissue together with the ablation lesions from the registered initial map.

3. The method according to claim 1, wherein the ablation lesions are produced by application of radio frequency (RF) energy to myocardial tissue in the chamber of the heart.

4. The method according to claim 1, wherein the initial map and the current map are acquired by inserting the probe into the chamber of the heart, and tracking coordinates of the probe while moving the probe within the heart.

5. A system for cardiac treatment, comprising:
a probe configured for insertion into a chamber of a heart of a patient; and
a processor, which is configured to receive an initial map of a chamber of a heart of a patient, acquired in an initial ablation procedure, with locations of ablation lesions marked on the initial map, and which is coupled to acquire a current map of the chamber using the probe in preparation for a redo ablation procedure, subsequent to the initial ablation procedure, and to register the initial map with the current map and to mark and display on the current map the locations of the ablation lesions from the registered initial map,
wherein the processor is configured to register the initial map by identifying at least one anatomical landmark in both the initial map and the current map, and aligning the at least one landmark identified in the initial map with a position of the at least one landmark identified in the current map,
wherein the chamber is a left atrium of the heart, and the at least one landmark comprises a carina between superior and inferior pulmonary veins connecting to the left atrium,
wherein the processor is adapted to superimpose on the current map wide circumferential ablation (WCA) lines produced in the initial ablation procedure, and wherein the redo ablation procedure comprises ablating further tissue in the chamber at sites chosen to close at least one conduction gap in the wide circumferential ablation (WCA) lines,
wherein the probe is configured to sense electrical activity in the chamber of the heart,
wherein the processor is configured to generate an electrical activity map and superimpose the electrical activity map on the surface of the current map,
wherein the electrical activity map is generated by sensing electrical activity in the left atrium using the probe,
wherein the electrical activity map provides information regarding the electrical activity,
wherein the processor is adapted to employ the information regarding the electrical activity in connection with the at least one anatomical landmark in both the initial map and the current map to determine locations of gaps in the wide circumferential ablation (WCA) lines,
wherein the processor is adapted to visualize an effect of further ablation lesions on the electrical activity.

6. The system according to claim 5, wherein the redo ablation procedure comprises ablating further tissue in the chamber, and wherein the processor is configured to mark and display on the current map the locations of further ablation lesions created by ablating the further tissue together with the ablation lesions from the registered initial map.

7. The system according to claim 5, wherein the ablation lesions are produced by application of radio frequency (RF) energy by the probe to myocardial tissue in the chamber of the heart.

8. The system according to claim 5, wherein processor is configured to acquire the current map by tracking coordinates of the probe while moving the probe within the heart.

9. A computer software product, comprising a computer-readable medium in which program instructions are stored, which instructions, when read by a processor, cause the processor to receive an initial map of a chamber of a heart of a patient, acquired in an initial ablation procedure, with locations of ablation lesions marked on the initial map, and to acquire a current map of the chamber in preparation for a redo ablation procedure, subsequent to the initial ablation procedure, and to register the initial map with the current map and to mark and display on the current map the locations of the ablation lesions from the registered initial map,
wherein the processor is configured to register the initial map by identifying at least one anatomical landmark in both the initial map and the current map, and aligning the at least one landmark identified in the initial map with a position of the at least one landmark identified in the current map, and wherein the chamber is a left atrium of the heart, and the at least one landmark comprises a carina between superior and inferior pulmonary veins connecting to the left atrium, wherein the processor is adapted to superimpose on the current map wide circumferential ablation (WCA) lines produced in the initial ablation procedure, and wherein the redo ablation procedure comprises ablating further tissue in the chamber at sites chosen to close at least one conduction gap in the wide circumferential ablation (WCA) lines, and wherein the processor is adapted to communicate with a probe, wherein the probe is configured to sense electrical activity in the chamber of the heart, wherein the processor is configured to generate an electrical activity map and superimpose the electrical activity map on the surface of the current map, wherein the electrical activity map is generated by sensing electrical activity in the left atrium using the probe, wherein the electrical activity map provides information regarding the electrical activity, wherein the processor is adapted to employ the information regarding the electrical activity in connection with the at least one anatomical landmark in both the initial map and the current map to determine locations of gaps in the wide circumferential ablation (WCA) lines, wherein the processor is adapted to visualize an effect of further ablation lesions on the electrical activity in the atrial wall.

* * * * *